United States Patent [19]

Higa

[11] Patent Number: 5,784,433
[45] Date of Patent: Jul. 21, 1998

[54] DENTAL X-RAY FILM PACKET STRUCTURE AND METHOD FOR CUSHIONING DENTAL X-RAY FILM PACKETS

[76] Inventor: Jack Higa, 974 Esquimalt Avenue, West Vancouver, British Columbia, Canada, V7T 1J8

[21] Appl. No.: 797,651

[22] Filed: Jan. 31, 1997

[51] Int. Cl.⁶ .................................................. A61B 6/14
[52] U.S. Cl. .................................... 378/168; 378/171
[58] Field of Search .............................. 378/168, 167, 378/171, 173, 184

[56] References Cited

U.S. PATENT DOCUMENTS

| | | | |
|---|---|---|---|
| 4,852,143 | 7/1989 | Scheier et al. | 378/168 |
| 5,450,465 | 9/1995 | Tanaka | 378/167 |

FOREIGN PATENT DOCUMENTS

| | | | |
|---|---|---|---|
| 0374361 | 6/1990 | European Pat. Off. | 378/168 |
| 2547014 | 5/1976 | Germany | 378/168 |

*Primary Examiner*—Don Wong
*Attorney, Agent, or Firm*—Lance A. Turlock

[57] ABSTRACT

A dental X-ray film structure includes a dental X-ray film packet in combination with a strip of soft, flexible cushion material. The strip moisture resistant includes a first portion adhered in partially overlapping engagement with a corresponding portion of one of the film packet surfaces along a selected edge of the packet, and a second portion contiguous with the first portion which extends outside the perimeter of the packet. The second portion serves to cushion the selected edge when the packet is positioned within the mouth of a dental patient for taking a dental X-ray. To completely cover the selected edge, the strip may include a third portion which is contiguous with the second portion, and which is adhered in partially overlapping engagement with a corresponding portion of the film packet surface opposite to the surface to which the first portion is adhered.

5 Claims, 2 Drawing Sheets

5,784,433

DENTAL X-RAY FILM PACKET STRUCTURE AND METHOD FOR CUSHIONING DENTAL X-RAY FILM PACKETS

FIELD OF THE INVENTION

This invention relates to the field of dental radiography and, in particular, to the structure of film packets used for the purpose of taking dental X-rays and methods for cushioning such packets.

BACKGROUND TO THE INVENTION

Radiography has long been considered an essential procedure for diagnosis and treatment in both dentistry and medicine. In dentistry, its practical use and application was recorded within a few months following publication of the discovery of X-rays.

Today, there is a wide application of radiography in dentistry. X-ray film packets of various shapes and sizes are used intra orally and extra orally to suit various situations. The most commonly utilized packets are intra oral, and perhaps the most common intra oral size is approximately 31×41 mm. This size has a more universal application (either as a bite wing film packet or as a periapical film packet) than other intra oral sizes which are less frequently used: for example, 27×54 mm, 24×40 mm, and 22×35 mm.

Herein, the words "X-ray film packet" are intended to mean an X-ray film alone and an X-ray film with or without a coating which is commonly used to protect the film. In the trade, the words "film packet" and "film" tend to be used interchangeably.

Generally, an operator (dentist or dental X-ray technician) will not encounter difficulty when positioning an intra oral film packet in an average sized mouth. However, to help hold a packet in proper alignment with a specific tooth, a block of foam material tapered or otherwise cut to meet the particular requirement on occasion will be adhered to a side surface of the packet. The taper or cut of the foam block is designed such that the axial line of the tooth extends parallel to the plane surface of the packet.

With or without the presence of a foam block on the side surface of a film packet, the sharp edges of the packet can cause a patient some distress by impinging on tissue within the mouth. Indeed, the problem is a source of frequent complaint from patients. The vulnerable areas include the floor of the mouth, the mucosa overlying the alveolar bone, the hard palate and the soft palate.

Typically, a patient will react to the pain by trying to avoid the discomfort, and may open or move his or her mouth without the operator's notice. As a result, the packet may move with a consequent distortion of the X-ray image and/or with a consequent insufficient recording of the desired field of view. Children with their small mouths are especially vulnerable to the sharp edges of X-ray film packets.

In an effort to ease the problem, X-ray film manufacturers have produced so-called soft packets (e.g. the Kodak Dental Products Division of Eastman Kodak Company, Rochester, N.Y., markets soft packets under the trademark POLY-SOFT). However, such packets cannot be forced into vulnerable areas of the mouth without eliciting pain.

Occasionally, an operator may endeavour to relieve the discomfort of a sharp edge by holding material such as gauze or the like over the edge while positioning the packet. However, this approach is awkward and unsatisfactory. It requires the operator to fuss with holding the gauze in position while the packet is positioned. The problem is compounded because the gauze can become saturated with saliva thereby making it slippery and less manageable. Another dimension is added for possible movement or slippage of the packet: viz. not only may the gauze with the packet slip against the tissue, but the packet may slip against the gauze. In either case, an unacceptable X-ray image may result. Moreover, there can be misadventure through inadvertent swallowing of the gauze.

Accordingly, it is a primary object of the present invention to provide a new and improved dental X-ray film structure which, in use, serves to reduce or avoid the pain and discomfort normally associated with the sharp edges of X-ray film packets when used intra orally.

A further object of the present invention is to provide a new and improved dental X-ray film structure of the foregoing type which is simple to construct and easy for the operator to use.

SUMMARY OF THE INVENTION

In accordance with one aspect of the present invention, there is provided a dental X-ray film structure comprising a dental X-ray film packet in combination with a moisture resistant strip of soft, flexible cushion material. As with typical intra oral packets, the packet is characterized by opposed first and second side surfaces and thin side edges extending transversely between the side surfaces. The side edges define the perimeter of the packet. Standard size, commercially available packets may be used.

The strip of cushion material includes a first portion adhered in partially overlapping engagement with a corresponding portion of one of the film packet surfaces along substantially the full length of a selected one of the edges, and a second portion contiguous with the first portion which extends outside the perimeter of the packet. The second portion serves to cushion the selected edge when the packet is positioned within the mouth of a dental patient for taking a dental X-ray.

With the present invention, the strip of cushion material preferably includes a third portion which is contiguous with the second or extended portion, and which is adhered in partially overlapping engagement with a corresponding portion of the other one of the film packet surfaces along the selected edge. Then, it will be assured the strip will remain in place covering the selected edge of the packet as the packet is positioned within the mouth of the patient. The manual dexterity required on the part of the operator is minimal because the entire structure can be quickly inserted in the mouth and adjusted to the desired position without having to grasp or manipulate the strip.

Less ideally, the portion of the strip which extends outside the perimeter of the film packet may extend loosely like a flap. In this case, the flap will be manually folded and held over the selected edge as the packet is positioned within the mouth of the patient. This approach requires some added dexterity because the operator must ensure that the flap is positioned to angle up and over rather than away from the edge during the positioning process. Nevertheless, it is an approach which can be managed relatively easily.

In accordance with another aspect of the present invention, there is provided a method for cushioning a selected edge of a dental X-ray film packet extending between opposed side surfaces of the packet, the method comprising the steps of exposing an adhesive surface of an elongated moisture resistant strip of soft, flexible cushion material; aligning the selected edge with the strip; while maintaining such alignment, adhering a first portion of the strip in overlapping partially engagement with a corresponding portion of one of the packet surfaces along substantially the full length of the selected edge while permitting a second portion of the strip contiguous with the first portion to extend outside the perimeter of the packet along the edge; then positioning the packet with the adhered strip within the mouth of the dental patient for the purpose of taking a dental X-ray while edges of the packet other than the selected edge remain uncushioned. Preferably, the method further includes the step of adhering a third portion of the strip contiguous with the second portion in partially overlapping engagement with a corresponding portion of the other one of the packet surfaces along the selected edge.

It has been found that the use of a strip of soft, flexible cushion material in the manner described serves not only to reduce or avoid the pain and discomfort normally associated with the sharp edges of X-ray film packets when used intra orally, but also to lessen or eliminate the gag reflex which can be initiated by the sharp edges of a film packet intruding itself in the soft palate area of the mouth.

The foregoing and other aspects of the present invention will now be further described with reference to the drawings. The specifics illustrated in the drawings are intended to exemplify, rather than limit, the invention as defined in the claims.

DETAILED DESCRIPTION OF PREFERRED EMBODIMENTS

Figure 1:
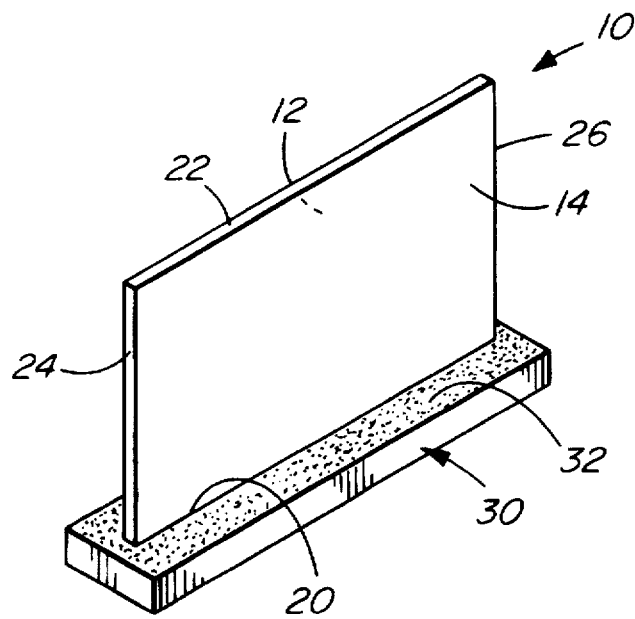
FIG. 1 is a perspective view illustrating a dental X-ray film packet and strip of cushion material in accordance with the present invention.

Referring now to the figures (which are not to scale), FIG. 1 illustrates a dental X-ray film packet generally designated 10 and an elongated strip of soft, flexible cushion material generally designated 30. As is described below in more detail, the purpose of the strip is to cushion a selected edge of the packet when the packet is positioned within the mouth of a dental patient for taking a dental X-ray.

Packet 10 has a conventionally sized overall rectangular shape including opposed first and second side surfaces 12, 14, and thin side edges 20, 22, 24 and 26 which extend transversely between the side surfaces and define the perimeter of the packet. Such packets are designed for intra oral usage and are commercially available from a variety of sources, for example: AGFA Gavaert AG., Leverkusen-Bayerwerk, Germany. As noted above, typical sizes for such packets would include 31 ×41 mm (probably the most common), and less common sizes such as 27 ×54 mm, 24×40 mm, and 22×35 mm. Typically, the thickness of such packets is about one mm.

In FIG. 1, the strip of cushion material 30 is shown in preparation to be used as a cushion for side edge 20 of packet 10 (edge 20 being the "selected" edge for purposes of the present illustration). As can be seen, the strip initially has an overall oblong shape and, although not essential, the length of the strip is slightly greater than the length of side edge 20. For example, if side edge 20 was 41 mm in length, then the length of strip 30 may be about 44 mm. This slightly greater length is preferable to allow not only edge 20 but also the relatively sharp corners formed between edge 20 and edges 24 and 26 to be covered by the strip.

Figure 2:
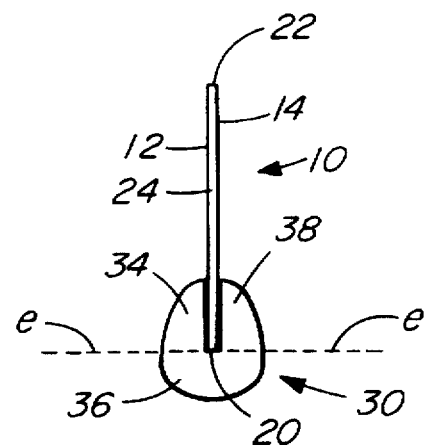
FIG. 2 is an end elevation view showing the strip of cushion material in FIG. 1 when folded over a selected edge of the packet to partially overlap both side surfaces of the packet.

The width of strip 30 (left to right in FIG. 1) is sized to permit the strip to partially overlap both side surfaces 12 and 14 of packet 10 when the strip is folded over edge 20 as shown in FIG. 2. Although not critical, it has been found that a width of about 10 mm is suitable. Likewise, and although again not critical, it has been found that a strip thickness (top to bottom in FIG. 1) of about 7 mm is suitable.

Surface 32 of strip 30 is covered with an adhesive for adhering the strip to packet 10. Thus, when the strip is positioned as shown in FIG. 1 and then folded upwardly over edge 20 on opposed sides of the packet as shown in FIG. 2, then a first portion 34 of strip 30 adheres in overlapping engagement with a corresponding portion of surface 12 of the packet along edge 20; a second portion 36 contiguous with the first portion 34 extends beyond edge 20 outside the perimeter of the packet; and a third portion 38 adheres in overlapping engagement with a corresponding portion of surface 14 of the packet along edge 20.

Second portion 36 of strip 30 outside the perimeter of packet 10 (viz. basically that portion which lies below line e—e in FIG. 2) serves to cushion edge 20 when packet 10 is placed within the mouth of a dental patient for taking a dental X-ray.

Apart from softness and flexibility, the material composition of strip 30 is not considered critical. With the addition of adhesive, one suitable material is that manufactured by the Voltek Division of Sekisui Corporation of America, Lawrence, Mass., U.S.A. under the trademark MINICEL. This material includes moisture resistant qualities and, as described by Voltek, is an extremely fine, closed cell, chemically cross-linked, polyolefin foam.

Adhesive is readily applied to such material using commercially available pressure sensitive adhesive (PSA) provided in rolls with a paper backing or liner. Typically, a bulk expanse of foam material sufficient for a large number of strips may be covered with PSA. Subsequently, the material can be easily cut to a size consistent with the dimensions of the edge of a packet to be cushioned. The paper backing can be easily peeled and removed immediately prior to use. One source of suitable PSA is 3M Canada Company, London, Ontario.

In use, a suitable X-ray film packet 10 is selected depending upon the X-ray to be taken. With adhesive surface 32 exposed, strip 30 is then longitudinally aligned with a selected edge 20 of the packet in the manner shown in FIG. 1. Then, while maintaining the longitudinal alignment, respective portions of the strip are adhered as shown in FIG. 2 to corresponding portions of packet surfaces 12 and 14 along edge 20. At first instance, a firm grip applied to press packet edge 20 against strip 30 will set the desired position with stickiness between the edge and the strip serving to hold the position. Then, using finger pressures, the strip can be easily folded over edge 20 and adhered to surfaces 12 and 14. The combined X-ray film packet and strip of cushion material is then ready for use.

Figure 3:
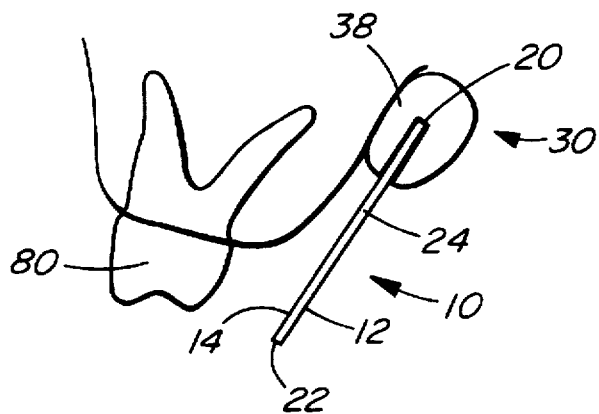
FIG. 3 is an elevation view showing maxilla positioning of the dental X-ray film packet and strip of cushion material shown in FIG. 2.
Figure 4:
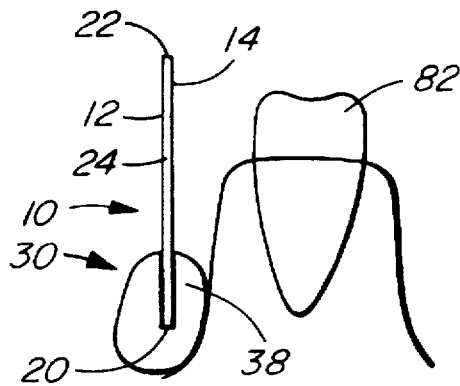
FIG. 4 is an elevation view showing mandibular positioning of the dental X-ray film packet and strip of cushion material shown in FIG. 2.

Examples of use are shown in FIGS. 3 and 4. FIG. 3 illustrates maxilla positioning of packet 10 with strip 30. This serves to cushion the mucosa of the hard palate (or occasionally the soft palate) against edge 20 while taking an X-ray of the maxillary first molar 80. Similarly, FIG. 4 illustrates mandibular positioning of packet 10 with strip 30 serving to cushion the mucosa of the sublingual surface of the oral cavity against edge 20 while taking an X-ray of the mandibular first molar 82.

In the arrangement shown in FIGS. 2, 3 and 4, it will be noted that strip 30 is adhered to both side surfaces 12 and 14 of film packet 10. Generally, this arrangement is considered preferable. However, a suitable cushioning effect may also be achieved if strip 30 is adhered to only one side surface of the film. By way of example, this is shown more particularly in FIG. 6.

Figure 6:
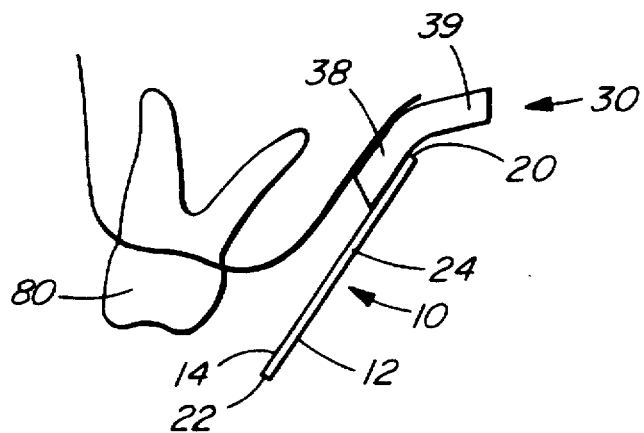
FIG. 6 is an elevation view showing maxilla positioning of the dental X-ray film packet and strip of cushion material shown in FIG. 5, the strip being adhered to only one side of the packet.

FIG. 6 depicts maxilla positioning similar to the case of FIG. 3. However, as can be seen in FIG. 6, only portion 38 of strip 30 is adhered in overlapping engagement with a corresponding portion of surface 14 of packet 10 along edge 20. A remaining or second portion 39 contiguous with portion 38 extends as a flap beyond edge 20 outside the perimeter of the packet. The flap serves to cushion the mucosa of the hard palate against edge 20 while taking an X-ray of the maxillary first molar 80 as described above. (It may be noted that the flap or portion of strip 30 defined as portion 39 in FIG. 6 is simply the combined portions defined as portions 34 and 36 in FIG. 2).

Figure 5:
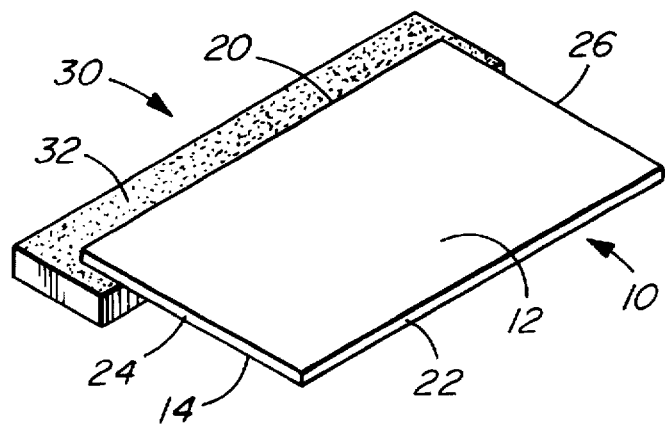
FIG. 5 is a perspective view illustrating a different initial juxtaposition of the film packet and strip of cushion material shown in FIG. 1.

For use in the manner shown in FIG. 6, adhesive surface 32 of strip 30 is exposed and the strip is initially aligned with selected edge 20 of the packet 10 in the manner shown in FIG. 5. Then, while maintaining such alignment, a firm pressure is applied to surface 12 across from that portion of surface 14 which overlaps with the strip. This pressure serves to adhere the packet to the strip. Then, the combined packet and strip of cushion material may be positioned in the patient's mouth, care being taken to ensure that portion 39 of the strip folds over rather than away from edge 20 of the packet.

It will be readily apparent to those skilled in the art that a variety of modifications, changes and variations to the invention are possible within the spirit and scope of the claims which follow. The invention should not be considered as restricted to the specific embodiments described and illustrated with reference to the drawings.

I claim:

1. A dental X-ray film structure, comprising:
   (a) a dental X-ray film packet having:
      (i) opposed first and second side surfaces; and
      (ii) thin side edges extending transversely between said side surfaces and defining the perimeter of said packet; and,
   (b) a moisture resistant strip of soft, flexible cushion material partially overlapping said first side surface along a selected one only of said edges, said strip including:
      (i) a first portion adhered in overlapping engagement with a corresponding portion of said first side surface along substantially the full length of said selected edge;
      (ii) a second portion contiguous with said first portion and extending laterally outside said perimeter for cushioning said selected edge when said packet is positioned within the mouth of a dental patient for taking a dental X-ray.

2. A dental X-ray film structure as defined in claim 1 wherein said strip additionally partially overlaps said second side surface, said strip including a third portion contiguous with said second portion, said third portion being adhered in overlapping engagement with a corresponding portion of said second side surface along said selected edge.

3. A dental X-ray film structure as defined in claim 1 or 2, wherein said strip has a length slightly greater than the length of said selected edge.

4. A method of cushioning a selected edge of a dental X-ray film packet having opposed first and second side surfaces and thin side edges extending transversely between said surfaces and defining the perimeter of said packet, said method comprising the steps of:
   (a) exposing an adhesive surface of an elongated, moisture resistant strip of soft, flexible cushion material;
   (b) aligning said selected edge with said strip,
   (c) while maintaining said alignment, adhering a first portion of said strip in partially overlapping engagement with a corresponding portion of one of said packet surfaces along substantially the full length of said selected edge while permitting a second portion of said strip contiguous with said first portion to extend laterally outside said perimeter along said edge; and,
   (d) then positioning said packet with said adhered strip within the mouth of a dental patient for the purpose of taking a dental X-ray while said edges other than said selected edge remain uncushioned.

5. A method as defined in claim 4, further comprising the step of adhering a third portion of said strip contiguous with said second portion in partially overlapping engagement with a corresponding portion of the other one of said packet surfaces along said selected edge.

* * * * *